(12) United States Patent
Chun

(10) Patent No.: US 6,406,686 B1
(45) Date of Patent: Jun. 18, 2002

(54) CONDITIONING SHAMPOO CONTAINING ARABINOGALACTAN

(75) Inventor: Ho-Ming Chun, Belmont, MI (US)

(73) Assignee: Amway Corporation, Ada, MI (US)

( * ) Notice: Subject to any disclaimer, the term of this patent is extended or adjusted under 35 U.S.C. 154(b) by 0 days.

(21) Appl. No.: 09/531,372

(22) Filed: Mar. 21, 2000

(51) Int. Cl.$^7$ .......................... A61K 7/075; A61K 7/08; A61K 7/06; A61K 7/11
(52) U.S. Cl. ............... 424/70.27; 424/70.1; 424/70.11; 424/70.12; 424/70.19; 424/70.21; 424/70.22; 424/70.31; 424/70.24
(58) Field of Search ............................ 424/70.1, 70.11, 424/70.12, 70.19, 70.21, 70.22, 70.27, 70.31, 70.24

(56) References Cited

U.S. PATENT DOCUMENTS

| | | | | |
|---|---|---|---|---|
| 3,728,447 A | * | 4/1973 | Osipow et al. | |
| 4,511,497 A | * | 4/1985 | Ehrlich | |
| 4,736,756 A | | 4/1988 | Grollier | 132/7 |
| 4,749,565 A | | 6/1988 | Grollier | 424/70 |
| 4,985,173 A | * | 1/1991 | Takahashi et al. | |
| 5,037,643 A | | 8/1991 | Green | 424/70 |
| 5,152,914 A | | 10/1992 | Forster et al. | 252/174 |
| 5,368,850 A | | 11/1994 | Cauwet et al. | 424/70 |
| 5,518,733 A | | 5/1996 | Lamothe et al. | 424/430 |
| 5,520,200 A | * | 5/1996 | Sturia | |
| 5,536,493 A | | 7/1996 | Dubief | 424/70.13 |
| 5,641,480 A | | 6/1997 | Vermeer | 424/70.24 |
| 5,747,014 A | | 5/1998 | Cauwet et al. | 424/70.11 |
| 5,747,297 A | * | 5/1998 | Clarke et al. | |
| 5,756,079 A | | 5/1998 | Cauwet et al. | 424/70.19 |
| 5,900,232 A | | 5/1999 | Cauwet et al. | 424/70.22 |
| 5,976,516 A | * | 11/1999 | Sakai et al. | |

OTHER PUBLICATIONS

Cosmetic and Toiletry Formulations (Noyes Publications Park Ridge, New Jersey, 1992), p. 371.*
Harry's Cosmeticology (Chemical Publishing 1982).*
Surfactant Encyclopedia, Cosmetics & Toiletries (Allured Publishing Feb. 1989).*
Remington's Pharmaceutical Sciences, Eighteenth Edition, pp. 1520–1521.*

* cited by examiner

Primary Examiner—Thurman K. Page
Assistant Examiner—Humera N. Sheikh
(74) Attorney, Agent, or Firm—Brinks Hofer Gilson & Lione

(57) ABSTRACT

A conditioning shampoo comprising a conditioning agent, a primary surfactant, and arabinogalactan, wherein the arabinogalactan suspends the conditioning agent.

22 Claims, No Drawings

CONDITIONING SHAMPOO CONTAINING ARABINOGALACTAN

The present invention is directed to a stable hair care composition and, in particular, to a stable conditioning shampoo comprising a conditioning agent, a primary surfactant, and arabinogalactan, wherein the arabinogalactan suspends the conditioning agent.

A major problem associated with formulating a shampoo containing silicone as a conditioning agent and a primary surfactant is that the silicone tends to separate out from the rest of the composition, resulting in two separate phases of the shampoo. This is functionally and aesthetically undesireable. For this reason, it has been proposed to use a suspending agent to prevent this phase separation. Usually, a shampoo must be fairly thick and have a fairly high viscosity for a suspending agent to be effective in preventing phase separations.

Surprisingly, it has been found that arabinogalactan suspends silicone in a shampoo even where that shampoo has a low viscosity.

SUMMARY OF THE INVENTION

Surprisingly, it has been found that a conditioning shampoo comprising a conditioning agent, a primary surfactant, and arabinogalactan provide a stable conditioning shampoo. Arabinogalactan is a sugar that acts as a suspending agent to suspend the conditioning agent in the shampoo. Arabinogalactan provides a stable suspension of silicone in a shampoo even where that shampoo has a low viscosity.

Because of the consistency and low viscosity of arabinogalactan, researchers can determine whether arabinogalactan effectively stabilizes an unthickened silicone-containing composition faster than they can determine the effectiveness of other suspending agents. It is possible to tell within days whether arabinogalactan will stabilize a silicone-containing composition, especially if that composition does not contain thickeners.

In one aspect, the present invention is a conditioning shampoo comprising a conditioning agent, a primary surfactant selected from the group consisting of anionic surfactants, amphoteric surfactants, and mixtures thereof, and arabinogalactan, wherein the arabinogalactan suspends the conditioning agent in the shampoo.

In another aspect, the present invention is a shampoo comprising 0.1% to about 20% by weight conditioning agent, from about 1% to about 80% by weight primary surfactant, and from about 0.1% to about 10% by weight arabinogalactan. It is noted that, unless otherwise stated, all percentages given in this specification and the appended claims refer to percentages by weight of the total shampoo.

The above and other aspects and advantages of the present invention will become apparent from the following detailed description of the preferred embodiments.

DETAILED DESCRIPTION OF THE PREFERRED EMBODIMENTS

In one embodiment of the present invention, the conditioning shampoo includes at least one conditioning agent, at least one primary surfactant, and arabinogalactan as a suspending agent, suspending the conditioning agent in the shampoo.

THE CONDITIONING AGENT

The conditioning agent is preferably a non-volatile silicone compound, a volatile silicone compound, or a mixture thereof.

The non-volatile silicones useful in the conditioning shampoo are polyalkyl siloxanes, polyalkylaryl siloxanes, polyether siloxane polymers, and silicone gums.

The non-volatile polyalkyl siloxanes that may be used in the shampoo include polydimethyl siloxanes with viscosities ranging from about 5 to 600,000 centistokes at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, Jul. 20, 1970. Preferably, the viscosity ranges from about 350 centistokes to about 100,000 centistokes.

The non-volatile polyalkylaryl siloxanes that may be used in the shampoo include polymethylphenylsiloxanes having viscosities of about 15 to 65 centistokes at 25° C. These siloxanes are available, for example, from the General Electric Company as SF 1075 methyl phenyl fluid or from Dow Corning as 556 Cosmetic Grade Fluid. Additionally, poly(dimethyl siloxane) (diphenyl siloxane) copolymers having a viscosity in the range of from about 10 to about 100,000 centistokes at 25° C. may be used.

Non-volatile polyether siloxane copolymers that may be used include a polypropylene oxide modified dimethylpolysiloxane (for example, Dow Corning DC-1248). Ethylene oxide or mixtures of ethylene oxide and propylene oxide may also be used in the shampoo.

References disclosing suitable silicones include Silicone Compounds distributed by Petrarch Systems, Inc., 1984, which is herein incorporated by reference.

Another silicone material that may be useful in the conditioning shampoo is a silicone gum. Silicone gums are described by Petrarch and others, including U.S. Pat. No. 4,152,416 to Spitzer et al. and Noll, Walter, *Chemistry and Technology of Silicones*, New York, Academic Press, 1986. General Electric Silicone Rubber Product Data Sheets SE 30, SE 33, SE 54, and SE 76 describe other silicone gums that may be useful. All of these references are incorporated herein by reference. "Silicone gum" materials denote high molecular weight polydiorganosiloxanes generally having a mass molecular weight of from about 200,000 to about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer, and mixtures thereof.

The non-volatile silicone compound is added to the shampoo in an amount sufficient to provide improved combing and improved softness to the hair. The preferred non-volatile silicone is dimethicone.

The volatile silicones useful in the shampoo are linear or cyclic low molecular weight polydimethylsiloxanes. It is believed that these volatile silicones provide lubrication and hair conditioning properties to wet hair and have sufficient volatility to slowly volatilize from the hair so that a residual buildup of silicone compound is not present on the dry hair.

One example of a linear, low molecular weight volatile polydimethylsiloxane compound that can be used in the present composition is hexamethyldisiloxane, available commercially under the trade name Dow Corning 200 Fluid. It has a viscosity of 0.65 cs, is highly volatile, is non-greasy, provides lubrication, and improves the overall combing properties of the hair. Examples of cyclic volatile polydimethylsiloxanes include but are not limited to the cyclomethicones such as octamethylcyclotetrasiloxane and decamethylcyclopentasiloxane. Other preferred volatile silicones include Dow Corning's 244, 245, 344, 346, and 1411.

The conditioning shampoo preferably includes from about 0.1% to about 20%, preferably from about 0.5% to about 5%, and more preferably from about 1% to about 2% by weight of a conditioning agent.

THE PRIMARY SURFACTANT

The primary surfactant useful in the conditioning shampoo of the present invention are selected from the group consisting of anionic surfactants, amphoteric surfactants, and mixtures thereof. Such surfactants are described in McCutcheon's Detergents, Emulsifiers and Surface Active Agents and Detergents (Vol. I and II) by Schwartz, Perry and Berch, and Handbook of Industrial Surfactants $2^{nd}$ ed. (Vol. 1 and II) by Gower. All of these references are incorporated herein by reference.

An anionic surfactant of the present invention can be any of the anionic surfactants known or previously used in the art of shampoo compositions. Suitable anionic surfactants include, but are not limited to, compounds in the classes known as alkyl sulfates, alkyl ether sulfates, alkyl ether sulfonates, alpha-olefin sulfonates, beta alkyloxy alkene sulfonates, alkyl arylsulfonates, alkyl carbonates, alkyl ether carbonates, alkyl ether carboxylates, succinamates, sulfosuccinates, sarcosinates, taurates, fatty acid taurides, sulfated monoglycerides, fatty acid amino polyoxyethylene sulfates, and isothienates and combination thereof.

Anionic surfactants that are particularly useful include alkyl and alkyl ether sulfates. The alkyl sulfates have the general formula $ROSO_3M$ and the alkyl ether sulfates have the general formula $R(C_2H_4O)_xOSO_3M$ wherein R is a $C_{10-20}$ alkyl or aklenyl group, x is from 1 to 10 and M is a water-soluble cation such as ammonium, potassium, sodium and triethanolamine. The alkyl ether sulfates useful in the present invention are condensation products of ethylene oxide and monohydric alcohols having from about 10 to about 20 carbon atoms. Preferably, R has 12 to 18 carbon atoms in both the alkyl and alkyl ether sulfates. The alcohols can be derived from fats, for example, coconut oil or tallow, or can be synthetic. Lauryl alcohol and straight chain alcohols derived from coconut oil are preferred herein. Such alcohols are reacted with up to 10, and especially 2, molar proportions of ethylene oxide, and the resulting mixture of molecular species having, for example, an average of 2 moles of ethylene oxide per mole of alcohol, is sulfated and neutralized.

An especially useful anionic surfactant is a mixture of a lauryl sulfate salt, a lauryl ether sulfate salt, and a lauroyl sarcosinate salt.

Amphoteric surfactants can be also be used in the shampoo. The term "amphoteric surfactant," as used herein, is intended to encompass zwitterionic surfactants, which are well known to those skilled in the art as a set of amphoteric surfactants. A wide variety of amphoteric surfactants can be used in the shampoo. Particularly useful are those that are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, for example, carboxy, sulfonate, sulfate, phosphate, or phosphonate.

Non-limiting examples of amphoteric surfactants useful in the conditioning shampoo of the present invention are disclosed in the text references cited above that have been incorporated by reference.

Preferred amphoteric or zwitterionic surfactants include betaines, sultaines, and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, stearyl bis-(2-hydroxypropyl) carboxymethyl betaine, oleyl d-methyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2-hydroxyethyl) sulfopropyl betaine, and amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone Poulenc).

Examples of other amphoteric surfactants that may be used in this shampoo are sodium 3-dodecylaminopropionate, N-alkyltaurines such as the one prepared according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378. Others include alkyl, preferably $C_{6-22}$ and most preferably $C_{8-12}$, amphoglycinates; alkyl, preferably $C_{6-22}$ and most preferably $C_{8-12}$, amphopropionates; and mixtures thereof.

The active primary surfactant is generally present in the shampoo at a level of from about 1% to about 80%, preferably from about 5% to about 60%, and more preferably from about 10% to about 50%.

The presence of a primary surfactant does not negate the possibility that a secondary surfactant may be included in the conditioning shampoo of the present invention. Secondary surfactants may be present in amounts that do not interfere with the ability of the arabinogalactan to suspend the conditioning agent in the shampoo. Typically, this means secondary surfactants can be no more than about 10% by weight of the composition, preferably no more than about 5% by weight. These secondary surfactants include nonionic surfactants and cationic surfactants. Non-limiting examples of these surfactants are in the text references cited above that have been incorporated by reference.

Nonionic surfactants that may be useful as secondary surfactants in the conditioning shampoo are those that can be broadly defined as condensation products of long chain alcohols, for example $C_{8-30}$ alcohols, with sugar or starch polymers, that is, glycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel).

Other useful nonionic surfactants include the condensation products of alkylene oxides with fatty acids such as alkylene oxide esters of fatty acids. These materials have the general formula $RCO(X)_n$ OH wherein R is a $C_{10-30}$ alkyl group, X is —$OCH_2$ $CH_2$— (derived from ethylene glycol or oxide) or —$OCH_2$ $CHCH_3$— (derived from propylene glycol or oxide), and n is an integer from about 6 to about 200. Other nonionic surfactants are the condensation products of alkylene oxides with 2 moles of fatty acids (alkylene oxide diesters of fatty acids). These materials have the general formula $RCO(X)_n$ OOCR wherein R is a $C_{10-30}$ alkyl group, X is —$OCH_2$ $CH_2$— (derived from ethylene glycol or oxide) or —$OCH_2$ $CHCH_3$— (derived from propylene glycol or oxide), and n is an integer from about 6 to about 100. Other nonionic surfactants are the condensation products of alkylene oxides with fatty alcohols (alkylene oxide ethers of fatty alcohols). These materials have the general formula $R(X)_n$ OR' wherein R is a $C_{10-30}$ alkyl group, X is —$OCH_2$ $CH_2$— (derived from ethylene glycol or oxide) or —$OCH_2$ $CHCH_3$— (derived from propylene glycol or oxide), and n is an integer from about 6 to about 100 and R' is H or a $C_{10-30}$ alkyl group.

Still other useful nonionic surfactants are the condensation products of alkylene oxides with both fatty acids and fatty alcohols wherein the polyalkylene oxide portion is esterified on one end with a fatty acid and etherified on the other end with a fatty alcohol. These materials have the general formula $RCO(X)_n$ OR' wherein R and R' are $C_{10-30}$ alkyl groups, X is —$OCH_2$ $CH_2$ (derived from ethylene glycol or oxide) or —$OCH_2$ $CHCH_3$— (derived from propylene glycol or oxide), and n is an integer from about 6 to about 100. Nonlimiting examples of these alkylene oxide derived nonionic surfactants include ceteth-6, ceteth-10, ceteth-12, ceteareth-6, ceteareth-10, ceteareth-12, steareth-6, steareth-10, steareth-12, PEG-6 stearate, PEG-10 stearate, PEG-100 stearate, PEG-12 stearate, PEG-20 glyceryl stearate, PEG-80 glyceryl tallowate, PEG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Other nonionic surfactants suitable for use in the conditioning shampoo include sugar esters and polyesters, alkoxylated sugar esters and polyesters, $C_{1-30}$ fatty acid esters of $C_{1-30}$ fatty alcohols, alkoxylated derivatives of $C_{1-30}$ fatty acid esters $C_{1-30}$ fatty alcohols, alkoxylated ethers of $C_{1-30}$ fatty alcohols, polyglyceryl esters of $C_{1-30}$ fatty acids, $C_{1-30}$ esters of polyols, $C_{1-30}$ ethers of polyols, alkyl phosphates, polyoxyalkylene fatty ether phosphates, fatty acid amides, acyl lactylates, and mixtures thereof.

Preferred among the nonionic surfactants are those selected from the group consisting of steareth-21, ceteareth-20, ceteareth-12, sucrose cocoate, steareth-100, PEG-100 stearate, and mixtures thereof.

Cationic surfactants useful as secondary surfactants in the conditioning shampoo include cationic ammonium salts such as quaternary ammonium salts, and amino-amides. Other useful cationic surfactants include those identified in U.S. Pat. No. 5,151,209, U.S. Pat. No. 5,151,210, U.S. Pat. No. 5,120,532, U.S. Pat. No. 4,387,090, U.S. Pat. No. 3,155,591, U.S. Pat. No. 3,929,678, U.S. Pat. No. 3,959,461, and Schwartz, et al., Surface Active Agents, Their Chemistry and Technology, New York: Interscience Publishers, 1949; all of these documents being incorporated herein by reference in their entirety.

ARABINOGALACTAN

The conditioning shampoo includes arabinogalactan. Arabinogalactan is a sugar derived from the Larch Tree (Larix occidentalis). Specifically, arabinogalactan is a naturally-occurring polysaccharide extracted from the unused portion of harvested Larch trees. Larch arabinogalactan is very pure, containing greater than 98% arabinogalactan. It has a molecular weight of about 20,000 Daltons.

Arabinogalactan is a highly branched polysaccharide having a galactan backbone with side chains of galactose and arabinose galactan. Preferably, the ratio of arabinose to galactose is from 1:10 to 10:1. More preferably, the ratio is from 1:3 to 1:10. Most preferably, arabinogalactan has a 1:6 ratio of arabinose to galactose. A particularly preferred arabinogalactan has the following structure:

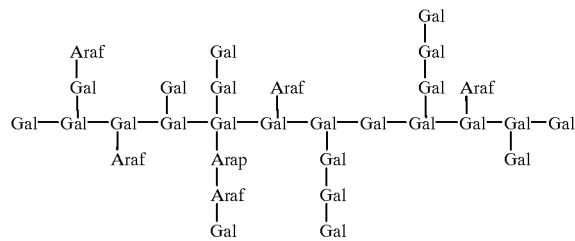

wherein "Gal" is galactose sugar in the galactopyranosyl form, "Araf" is arabinose sugar in the arabinofuranosyl form, and "Arap" is arabinose sugar in the arabinopyranosyl form.

Galactose, a monosaccharide, has this structure:

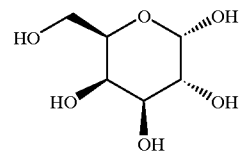

Galactose exists in equilibrium with its cyclic hemiacetal isomers. Galactofuransyl is the isomer containing a five-membered ring, and Galactopyranosyl is the isomer containing a six-membered ring.

Arabinose, a monosaccharide, has this structure:

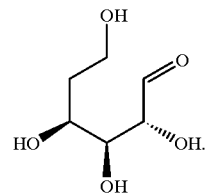

Arabinose exists in equilibrium with its cyclic hemiacetal isomers. Arabinofuransyl is the isomer containing a five-membered ring, and Arabinopyranosyl is the isomer containing a six-membered ring.

The preferred arabinogalactan is soluble in cold water. When dissolved, it forms a clear aqueous solution. The preferred arabinogalactan does not add substantial viscosity to the system. That is, adding arabinogalactan does not increase the viscosity of a silicone-containing system more than about 5%. Preferably, adding arabinogalactan does not increase the viscosity of a silicone-containing system by more than about 3%, more preferably about 1%. Further, the preferred arabinogalactan is stable in a variety of heat conditions, pH conditions, as well as being stable in the present of certain salts.

Generally, arabinogalactan is present in the shampoo in an amount effective to suspend the silicone material in the shampoo so that the shampoo remains stable at 120° F. for at least 30 days. The arabinogalactan is present in the shampoo in an amount from about 0.1% to about 10%, preferably from about 0.5% to about 5%, and most preferably from about 1% to about 4%. Ideally, arabinogalactan is present in the shampoo in an amount of about 2%.

OPTIONAL INGREDIENTS

The conditioning shampoo may include optional, additional suspending agents. Examples of additional polymeric suspending agents useful in the composition and method of the present invention include acrylate copolymer and acrylate/steareth-20 methacrylate copolymer, which is a polymer of the ester of methacrylic acid and steareth-20 and one or more monomers of acrylic acid, methacrylic acid or one of their simple esters. One useful suspending agent is an acrylate copolymer sold under the trade name Acculyn® 33 by Rohm and Haas Company of Philadelphia, Pa. Especially useful is acrylate/steareth-20 methacrylate copolymer sold under the trade name Aculyn® 22 also by Rohm and Haas.

The shampoo can include other optional, compatible ingredients so long as those ingredients do not detract from the advantageous results of the present invention. Typically, such additional ingredients are included in an aggregate amount of less than about 10%, typically less than about 5%, and preferably less than about 3.50%. Optional ingredients may include secondary surfactants as described above, proteins, vitamins (including vitamins A, C, E, and K), salt, botanical extracts (including include balm mint, birch, chamomile, fir, heather, honey suckle, ivy, jasmine, lotus, pine, rose, soapwort, violet willow bark, winter green, witch hazel, and yucca), dyes, preservatives, fragrance, buffering agents and ceramides, pseudoceramides, alpha or beta hydroxy acids, and the like.

When completely formulated, the shampoos should have a cosmetically-acceptable viscosity. Preferably, the viscosity range should be from 1000 to 10000 cps, more preferably from 4000 to 8000 cps.

For shampoo development purposes, to test the arabinoglacatan as a suspending agent, the test samples and control samples should have a much lower viscosity than that of a final product. The test and control samples should have a viscosity of less than 3000 cps, preferably less than 2000 cps, and more preferably less than 1000 cps. Previously, it was difficult for a suspending agent to be effective in a shampoo having a viscosity this low. Previously, for a suspending agent to be effective, shampoos had viscosities higher than 2000 cps.

Because of its consistency as well as its low viscosity, researchers can determine whether arabinogalactan effectively stabilizes an unthickened silicone-containing composition surprisingly faster than they can determine the effectiveness of other suspending agents. It is possible to tell within days whether arabinogalactan will stabilize a silicone-containing composition, especially if that composition does not contain thickeners. In contrast, thicker, higher viscosity suspending agents can require weeks to determine effectiveness, even without the addition of thickeners.

The following non-limiting example illustrates a test sample of shampoo made in accordance with the present invention:

EXAMPLE

| INGREDIENTS | WEIGHT PERCENT |
| --- | --- |
| sodium lauryl sulfate (30% active) | 28.00 |
| sodium laureth sulfate (30% active) | 20.00 |
| dimethicone | 1.50 |
| arabinogalactan | 2.00 |
| ethylene glycol distearate | 1.25 |
| cocamide MEA | 2.00 |
| sodium chloride | 0.50 |
| preservative | 0.05 |
| citric acid | 0.01 |
| purified water | 44.69 |
| TOTAL | 100.00 |

In the example, the arabinogalactan was added to the shampoo base, which comprised all of the above-named ingredients. The pH was adjusted to 6.50 by adding citric acid. The viscosity of the resulting solution was less than 1000 cps. The stability of conditioning shampoo of the example was qualitatively compared to a control shampoo having all the same ingredients except for the arabinogalactan. The conditioning shampoo of the example was consistently more stable.

Of course, it should be understood that a wide range of changes and modifications can be made to the embodiments described above. It is intended, therefore, that the foregoing description illustrates rather than limits this invention, and that it is the following claims, including all equivalents, that define this invention.

What is claimed is:

1. A conditioning shampoo comprising:
   a) a conditioning agent,
   b) a primary surfactant selected from the group consisting of anionic surfactants, amphoteric surfactants, and mixtures thereof, the primary surfactant being present in the shampoo in an amount sufficient to cleanse hair; and
   c) arabinogalactan, wherein the arabinogalactan suspends the conditioning agent.

2. The conditioning shampoo of claim 1 wherein the conditioning agent is selected from the group consisting of volatile silicone-containing compositions, non-volatile silicone-containing compositions, and mixtures thereof.

3. The conditioning shampoo of claim 1 wherein the conditioning agent is selected from the group consisting of polyalkyl siloxanes, polyaryl siloxanes, polyalkylaryl siloxanes, and mixtures thereof.

4. The conditioning shampoo of claim 1 wherein the conditioning agent is selected from the group consisting of dimethicone, cyclomethicone, and mixtures thereof.

5. The conditioning shampoo of claim 1 wherein the primary surfactant is anionic.

6. The conditioning shampoo of claim 5 wherein the primary surfactant is selected from the group consisting of an alkyl sulfate, an alkyl ether sulfate, a sulfate ester of an alkylphenoxy polyoxyethylene ethanol, an alpha-olefin sulfonate, a beta-alkoxy alkane sulfonate, an alkyl aryl sulfonate, an alkyl carbonate, a sulfosuccinate, an alkyl ether sulfosuccinate, a sacristan, an octoxynol phosphate, a nonoxynol phosphate, a taurate, a fatty tauride, a sulfated monoglyceride, a fatty acid polyoxyethylene sulfate, an isethienate, and mixtures thereof.

7. The conditioning shampoo of claim 5 wherein the primary surfactant is a long chain alkyl sulfate having the formula ROSO$_3$M wherein R is an alkyl or alkenyl of about 10 to about 20 carbon atoms and M is a water-soluble cation.

8. The conditioning shampoo of claim 5 wherein the primary surfactant is selected from the group consisting of sodium lauryl sulfate, sodium laureth sulfate, and mixtures thereof.

9. The conditioning shampoo of claim 1 wherein the arabinogalactan has a ratio of arabinose to galactose of from 1:10 to 10:1.

10. The conditioning shampoo of claim 1 wherein the arabinogalactan has a ratio of arabinose to galactose of from 1:3 to 1:10.

11. The conditioning shampoo of claim 1 further comprising a secondary surfactant wherein the secondary surfactant is nonionic or cationic.

12. A conditioning shampoo comprising:
 a) from about 0.1% to about 20% conditioning agent,
 b) from about 5% to about 80% primary surfactant, and
 c) from about 0.1% to about 10% arabinogalactan, wherein the arabinogalactan suspends the conditioning agent.

13. The conditioning shampoo of claim 12 wherein the conditioning agent is a non-volatile silicone.

14. The conditioning shampoo of claim 12 wherein the primary surfactant is anionic.

15. The conditioning shampoo of claim 14 wherein the primary surfactant is a mixture of alkyl sulfates.

16. The conditioning shampoo of claim 12 further comprising less than about 5% of a non-ionic surfactant or a cationic surfactant, or a mixture thereof.

17. A conditioning shampoo comprising:
 a) from about 0.1% to about 20% dimethicone,
 b) from about 5% to about 80% sodium lauryl sulfate,
 c) from about 5% to about 80% sodium laureth sulfate, and
 d) from about 0.1% to about 10% arabinogalactan, wherein the
arabinogalactan suspends the conditioning agent.

18. A method of suspending a conditioning agent in a shampoo comprising adding an effective amount of arabinogalactan to the shampoo.

19. In a conditioning shampoo, the improvement comprising an effective amount of arabinogalactan in the shampoo to suspend a conditioning agent in the shampoo.

20. The conditioning shampoo of claim 1 having a pH$\geq$6.5.

21. The conditioning shampoo of claim 12 having a pH$\geq$6.5.

22. The conditioning shampoo of claim 17 having a pH$\geq$6.5.

* * * * *